(12) United States Patent
Bourlion et al.

(10) Patent No.: US 7,580,743 B2
(45) Date of Patent: Aug. 25, 2009

(54) DEVICE FOR MONITORING PENETRATION INTO ANATOMICAL MEMBERS

(75) Inventors: Maurice Bourlion, Saint-Chamond (FR); Alain Vanquaethem, Rognes (FR)

(73) Assignee: Spineguard, Paris (FR)

( * ) Notice: Subject to any disclaimer, the term of this patent is extended or adjusted under 35 U.S.C. 154(b) by 0 days.

(21) Appl. No.: 10/504,462

(22) PCT Filed: Feb. 11, 2003

(86) PCT No.: PCT/FR03/00440

§ 371 (c)(1),
(2), (4) Date: Feb. 8, 2005

(87) PCT Pub. No.: WO03/068076

PCT Pub. Date: Aug. 21, 2003

(65) Prior Publication Data

US 2005/0119660 A1   Jun. 2, 2005

(30) Foreign Application Priority Data

Feb. 11, 2002   (FR) .................................. 02 01652

(51) Int. Cl.
*A61B 5/05* (2006.01)
*A61B 17/00* (2006.01)
(52) U.S. Cl. ........................................ 600/547; 606/80
(58) Field of Classification Search ................ 600/547, 600/590; 606/79, 80
See application file for complete search history.

(56) References Cited

U.S. PATENT DOCUMENTS

| | | | |
|---|---|---|---|
| 4,243,388 A * | 1/1981 | Arai .............................. 433/27 |
| 4,365,637 A * | 12/1982 | Johnson ...................... 600/547 |
| 4,595,019 A | 6/1986 | Shene et al. |
| 4,630,615 A | 12/1986 | Yomtov |
| 4,697,599 A * | 10/1987 | Woodley et al. ............. 600/547 |
| 4,940,060 A * | 7/1990 | Gu et al. ...................... 600/548 |
| 5,001,436 A * | 3/1991 | Scot et al. .................... 324/689 |
| 5,300,108 A * | 4/1994 | Rebell et al. ................. 607/127 |
| 5,404,877 A * | 4/1995 | Nolan et al. ................. 600/484 |
| 5,482,052 A * | 1/1996 | Lerner ......................... 600/547 |
| 5,560,372 A * | 10/1996 | Cory ........................... 600/554 |
| 5,732,710 A * | 3/1998 | Rabinovich et al. ......... 600/547 |
| 5,902,105 A * | 5/1999 | Uejima et al. ................. 433/27 |
| 6,123,677 A * | 9/2000 | Heitmann et al. ........... 600/559 |

(Continued)

FOREIGN PATENT DOCUMENTS

DE   197 58 110 A1   7/1999

(Continued)

*Primary Examiner*—Max Hinenburg
*Assistant Examiner*—Jonathan M Foreman
(74) *Attorney, Agent, or Firm*—Bachman & LaPointe, P.C.

(57) ABSTRACT

The invention relates to a device that can be used to monitor the penetration of a penetration member into anatomical structures and, in particular, bone structures of a living body, the structures having at least two different electrical impedance areas. The device is characterized in that it comprises: at least one impedance meter which can be connected to at least two electrodes, at least one of the electrodes being located at a distal end of the penetration member; and at least one alert device which can produce an alert signal if the impedance meter detects an impedance variation. The invention also relates to a penetration member for the device and to an electronic board for the device.

28 Claims, 3 Drawing Sheets

U.S. PATENT DOCUMENTS

| | | | |
|---|---|---|---|
| 6,265,978 B1* | 7/2001 | Atlas | 340/575 |
| 6,337,994 B1* | 1/2002 | Stoianovici et al. | 600/547 |
| 6,391,005 B1* | 5/2002 | Lum et al. | 604/117 |
| 6,507,755 B1* | 1/2003 | Gozani et al. | 600/547 |
| 6,571,124 B1* | 5/2003 | Storm | 600/547 |
| 6,718,199 B2* | 4/2004 | Thornton | 600/544 |
| 6,823,212 B2* | 11/2004 | Pinyayev | 600/547 |
| 6,845,264 B1* | 1/2005 | Skladnev et al. | 600/547 |
| 6,847,841 B1* | 1/2005 | El Hatw | 600/547 |
| 6,980,852 B2* | 12/2005 | Jersey-Willuhn et al. | 600/547 |
| 2001/0020138 A1* | 9/2001 | Ishigooka et al. | 600/547 |
| 2002/0035339 A1* | 3/2002 | Kavet et al. | 600/547 |
| 2002/0161312 A1* | 10/2002 | Campbell et al. | 600/547 |
| 2003/0004431 A1* | 1/2003 | Pinyayev | 600/547 |
| 2003/0018279 A1* | 1/2003 | Rosenblatt | 600/547 |
| 2003/0088186 A1* | 5/2003 | Doody | 600/547 |
| 2003/0187366 A1* | 10/2003 | Hashimshony | 600/547 |
| 2003/0199782 A1* | 10/2003 | Gozani et al. | 600/547 |
| 2003/0216663 A1* | 11/2003 | Jersey-Willuhn et al. | 600/547 |
| 2004/0054298 A1* | 3/2004 | Masuo et al. | 600/547 |
| 2004/0077944 A1* | 4/2004 | Steinberg et al. | 600/436 |
| 2005/0119660 A1* | 6/2005 | Bourlion et al. | 606/80 |
| 2005/0234308 A1* | 10/2005 | Naukkarinen | 600/300 |

FOREIGN PATENT DOCUMENTS

| | | |
|---|---|---|
| FR | 2.101.911 | 3/1972 |
| FR | 2 691 623 A1 | 12/1993 |
| GB | 2 335 990 A | 10/1999 |
| WO | WO 01/01875 A1 | 1/2001 |

* cited by examiner

DEVICE FOR MONITORING PENETRATION INTO ANATOMICAL MEMBERS

BACKGROUND OF THE INVENTION (1) Field of the Invention

The present invention relates to the field of the penetration of material, such as bone structures or the like, that exhibit differences in intrinsic physical quantities.

The present invention relates more particularly to a device for monitoring the penetration of a penetrating means into anatomical structures, and especially bone structures, of a living body, said structures having at least two regions of different electrical impedance.

(2) Prior Art

In spinal surgery, for example, when drilling the pedicle, it frequently happens that the vertebral bone cortex is pierced, broken or chipped by the penetrating drill bit. Depending on the authors, 15 to 40% of pedicle screws are thus improperly positioned, with a clinical manifestation (pain, paralysis, hemorrhaging, etc.) in 1 to 2% of the cases and therefore require further intervention.

Surgeons sometimes use equipment such as the following:
equipment for surgical navigation, which is expensive and cumbersome to implement;
equipment for monitoring of sensory and/or motor evoked potentials, this being less expensive but also restricting as it requires the presence of a specialist whose mission is solely to carry out this monitoring operation.

As a result, in most cases the operators rely solely on their knowledge of anatomy and their experience in order to accomplish this risky surgical procedure.

The foregoing is also true in the case of other surgical fields.

In the field of drilling bone bodies, the prior art also includes international patent application WO 01/01875.

This patent application discloses a device that uses the ability of nerves and muscles to transmit signals, in order to warn the user when the drilling means comes into contact with a nerve, so as to prevent any lesion of said nerve.

The prior art also teaches the use of impedance measurement in medical devices.

For example, the prior art includes the United States Patent U.S. Pat. No. 4,630,615 which relates to a neural stimulation system that incorporates an apparatus for measuring or determining impedance in which it is desired to manage and determine the changes in impedance in a guide connected to a cathode implanted into the epidural space of a spinal column. Such a neural stimulation system is typically used when it is desired to block off pain signals that are sent to the brain, which system may also be used for the treatment and/or relief of symptoms involving uncoordinated movements of the spinal column, such as epilepsy, spasticity, cerebral paralysis, etc.

The prior art also includes British Patent Application GB 2 335 990 that relates to a system for mechanical penetration of a needle and for stopping the penetration if a different impedance is detected at the end of the needle.

The object of that system is to inform the user when the end of the needle has definitely reached the desired depth, either using an impedance value or using a change in impedance.

The object of that system is thus absolutely not to prevent a determined depth being reached.

Furthermore, that system requires, for each patient, an experimental determination of the impedance values or of the changes in impedance, as explained on the last page of that application, which absolutely does not allow this system to be adapted for the purpose of preventing a determined depth being reached.

The prior art also includes French Patent Application FR 2 101 911 which relates to an instrument for measuring the length of the root canal of a tooth.

That instrument is used to deduce the length of a hollow body by the subsequent measurement of the distance between two reference marks after these two reference marks have been placed into longitudinal abutment, respectively in the bottom of the tooth canal in the case of the probe, and the crown or the upper edge of the cavity in the case of the rubber piece.

That instrument allows the user to be informed, after having made a cavity, about the depth of this cavity; it does not allow real-time monitoring of the penetration of a penetrating means into anatomical structures.

Another drawback of the techniques of the prior art is that are cumbersome to implement and tend to extend the operation time, thus increasing the associated risks.

SUMMARY OF THE INVENTION

The present invention aims to remedy the drawbacks of the prior art by proposing a device that allows real-time monitoring of the penetration of the penetrating means (the drilling means or the like) into the material, by measuring the differences in a physical quantity as the penetration proceeds, so as to allow the user to know where the end of the penetrating means is and thus prevent any lesion.

The physical quantity used is the electrical impedance measurement.

It is important to point out that the use of the electrical impedance measurement may be applied to many different technical fields and not only to the field of drilling bony bodies.

The present invention relates, in its widest sense, to a device for monitoring the penetration of a penetrating means as claimed in claim 1.

This device includes at least:
at least one impedance meter that can be connected to at least two electrodes, at least one of which is located at a distal end of said penetrating means, said impedance meter continuously measuring the impedance between the two electrodes at least during the penetration; and
at least one warning device capable of producing a warning signal in the event of a change in impedance being detected by the impedance meter.

In one embodiment, the device further includes an electrostimulator capable of producing a stimulation and able to be connected to at least two electrodes, at least one of which is located at a distal end of said penetrating means.

In this embodiment, at least one electrode able to be connected to an electrostimulator and at least one electrode able to be connected to an impedance meter are preferably connected together. Thus, it is the same electrodes that serve both for delivering the neuromuscular stimulation and for measuring the impedance.

Throughout the text that follows, the term "distal end" is understood to mean, of course, as in the case of any surgical instrument, the end with respect to the handle used for holding the instrument, which is located at the proximal end.

Said warning signal is preferably a visual and/or audible and/or tactile signal.

The neuromuscular stimulation produced by the neuromuscular electrostimulator preferably has a frequency of less than or equal to 10 Hz, a voltage of less than or equal to 4 volts and a pulse of duration of less than or equal to 400 μs.

In one embodiment, an electrode is formed by a contact surface located at the distal end of said penetrating means and another electrode is formed by a contact surface intended to be positioned on an external surface of the anatomical structures.

In another embodiment, said electrodes are each formed by a contact surface respectively located at the distal end of said penetrating means, said contact surfaces being separated by an insulator.

In one version of this embodiment, the proximal electrode has a contact surface greater in area than the contact surface of the distal electrode.

In one embodiment, at least one distal electrode is formed by a contact surface located on a partial peripheral portion of the distal end of the penetrating means so as to make it possible to detect a change in impedance in a direction approximately perpendicular to the axis of penetration of the penetrating means.

The device according to the invention preferably includes means for rotating said penetration means.

In one version of the invention, the impedance meter, the warning device and optionally the electrostimulator are positioned on a removable electronic card, which includes means for connecting said electrodes, so as to allow the device to be sterilized independently of the electronic part.

The device according to the invention preferably includes, for this purpose, a hollow handle for accommodating said electronic card.

The present invention also relates to:
a fixed penetrating means, and especially a probe, squared tip, spatula or curette, or
a penetrating means that can be rotated, and especially a drill screw, drill tap or drill bit
for a device according to the invention.

The present invention also relates to an electronic card as defined above for a device according to the invention.

This electronic card is preferably able to be sterilized and, also preferably, is placed in a casing that preserves sterility.

The present invention further relates to a manual or motor-operated drilling instrument, especially for drilling the vertebral pedicle, said instrument including a penetrating means and a device for monitoring the penetration of said penetrating means according to the invention.

Advantageously, the present invention allows the user to be informed in real time of the progression of the penetrating means optionally associated with the drilling instrument.

Also advantageously, the electrode located upstream of the penetration is positioned close to the mechanical penetration effect and thus makes it possible to obtain a very high sensitivity in detecting a change in impedance.

Advantageously, the invention thus makes it possible to avoid complete transpiercing of the body to be penetrated or pierced, when this is not desired, and in the case of penetration of a bone body, to prevent a lesion of the tissues located beneath the bone body.

BRIEF DESCRIPTION OF THE DRAWINGS

The invention will be more clearly understood with the aid of the description, given below purely by way of explanation, of one embodiment of the invention, with reference to the appended figures.

DETAILED DESCRIPTION OF THE PREFERRED EMBODIMENT(S)

Figures 1, 2, 3:
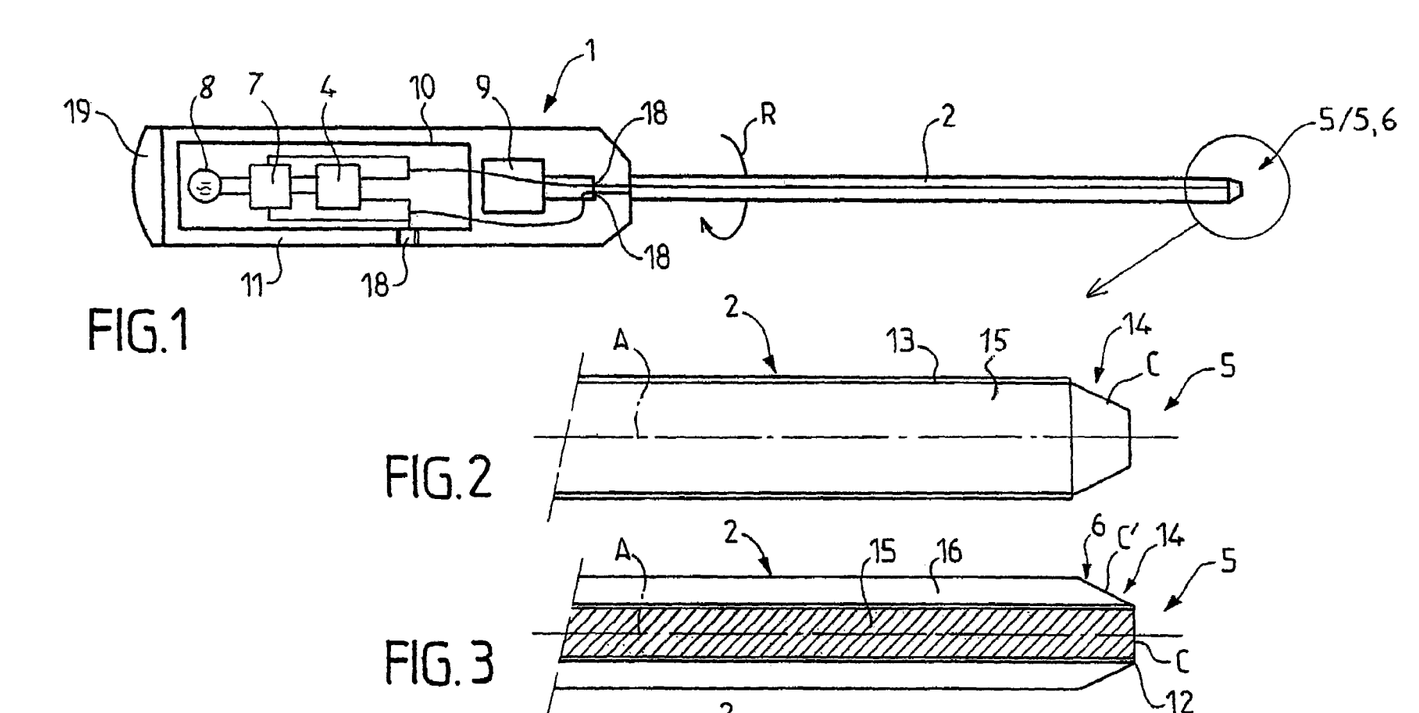
FIG. 1 illustrates a partial sectional view of an instrument fitted with a device according to the invention.
FIG. 2 illustrates a detailed sectional view of a first embodiment of the penetrating means in the form of a probe.
FIG. 3 illustrates a detailed sectional view of a version of the second embodiment of the penetrating means in the form of a probe.

The device (1) according to the invention, illustrated in FIG. 1, is a device for monitoring the penetration of a penetrating means (2) into anatomical structures, and especially bone structures (3) of a living being, said structures having at least two regions of different electrical impedance (Z1, Z2).

For example, the penetrating means (2) makes it possible, itself or combined with a drilling instrument, to drill a hole (20) in said bone structures (3).

A bone body is composed of soft internal tissue (marrow, spongy bone) and hard external tissue (cortex); it is itself surrounded by soft tissues: muscles, tendons, ligaments, blood vessels and nerves.

Owing to these differences in nature, the bone cortex has physical properties different from those of the tissues with which it is contact: it is for this reason that it is also visible in medical images: conventional radiography, scanner, echography, magnetic resonance imaging.

If the instrument used to penetrate the bone cortex is fitted at its distal end with a means for detecting and indicating this difference in physical properties, the operator will therefore immediately have information informing him that he has passed through this cortex or that he is about to do so.

However, it turns out that the bone cortex and the soft tissues also have different impedances.

In a base version, the device (1) according to the invention comprises:
at least one impedance meter (7) that can also be connected to at least two electrodes, at least one of which is located at a distal end of said penetrating means (2), said impedance meter continuously measuring the impedance between the two electrodes at least during the penetration; and
at least one warning device (8) capable of producing a warning signal in the event of a change in impedance being detected by the impedance meter (7).

Thus, thanks to the impedance meter (7), it is possible to monitor the penetration of the detection means associated with the penetrating means (2) progressively as the latter penetrates into the bone structures (3).

The way in which the impedance meter or meters (7) are used to deduce therefrom the position of the associated detection means constitutes one particular method of monitoring the penetration of a penetrating means (2) through a body having at least two regions of different electrical impedance (Z1, Z2).

The device (1) includes a warning device (8) which can emit:
- a visual warning signal modulated, for example, by the use of a flashing warning lamp or a ramp of warning lamps; and/or
- an audible warning signal frequency-modulated and possibly intensity-modulated, for example by the use of a loudspeaker; and/or
- A tactile warning signal frequency-modulated and possibly intensity-modulated, for example by the use of a vibrator, providing a warning right from the start of the change in measured impedance and when a threshold of a change in measured impedance is exceeded.

This modulated warning signal is proportional to the change in impedance.

This warning device (8) is preferably positioned on or in the instrument, as may be seen in FIG. 1.

The device (1) may optionally further include a display means for displaying the change or changes in impedance, which is connected to an impedance meter (7). This display means, formed for example by a display screen, makes it possible to monitor the variation, in the form of curves, of the change in impedance progressively with the penetration of the penetrating means (2).

In one embodiment, the device (1) further includes at least one electrostimulator (4), preferably a neuromuscular stimulator, capable of producing a preferably neuromuscular stimulation and able to be connected to at least two electrodes (5, 6), at least one of which is located at a distal end of said penetrating means (2).

The neuromuscular stimulation produced by the neuromuscular electrostimulator has:
- a frequency of less than or equal to 10 Hz, preferably around 2.5 Hz;
- a voltage of less than or equal to 4 volts, preferably around 1 volt; and
- a pulse of duration of less than or equal to 400 µs, preferably around 150 µs.

In the event of the bone cortex being penetrated by the penetrating means, the distal portion (tip) of the latter comes into contact with the soft tissues located on the outside of the cortical envelope. The stimulation pulses may then propagate easily into these soft tissues of low impedance and stimulate the nerves possibly located near the tip of the penetrating means. Two situations then arise:

a) if they are motor nerves, they will then cause contractions of the muscle groups with which they are associated, at the rate of the stimulation pulses; these contractions will be detected and recognized, either by an electromyography connected up to the patient beforehand, or clinically by the operator himself in relation to the patient's movements;

b) if they are sensory nerves, a suitable device will be able to detect their stimulation, which is also recognizable by its rate.

In a preferred version of the invention, the electrodes (5, 6) may be connected, using connection terminals (18), both to the electrostimulator (4) and to the impedance meter (7). Thus, it is the same electrodes that serve both for the emission of the neuromuscular stimulation and for the impedance measurement.

The penetrating means (2) of the device (1) may be:
- either fixed, and consisting especially of a probe, a squared tip, a spatula or a curette;
- or capable of being rotated, and consisting especially of a drill screw, a drill tap or a drill bit.

In the latter case, the device (1) then includes drive means (9) for the rotation R of said penetrating means (2).

The drive means (9) consist, for example, of an electric motor capable of rotating the penetrating means (2) and form, in combination with the penetrating means (2), a boring instrument (1) of the borer type.

In the section below, the penetrating means (2) is formed by a probe, but the configurations presented are applicable to any type of penetrating means (2).

Figure 5:
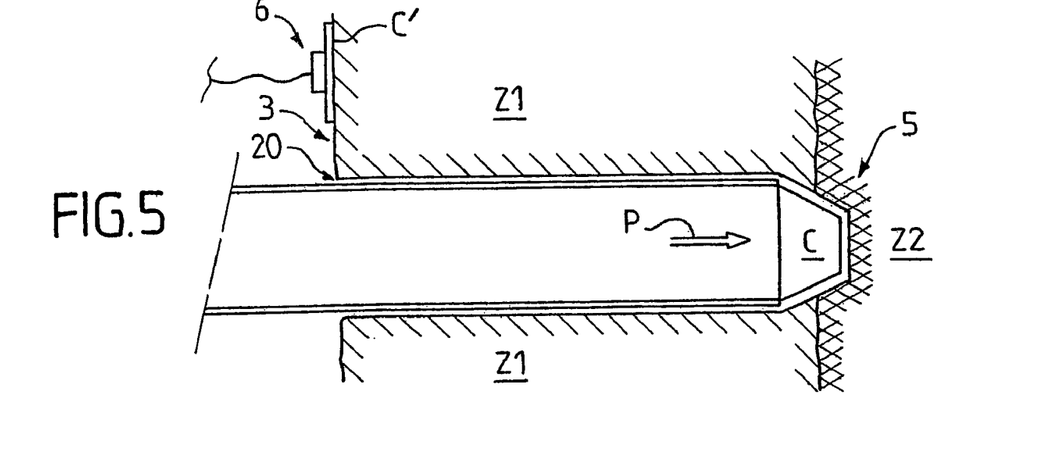
FIG. 5 illustrates a sectional view of the penetration P of the penetrating means of FIG. 2.

In a first embodiment, illustrated in FIGS. 2 and 5, a distal electrode (5) is formed by a contact surface C located at the distal end of said penetrating means (2) and another, proximal electrode (6) is formed by a contact surface C' intended to be positioned on an outer surface of the anatomical structures, including on the operation incision.

The penetrating means (2) has a central portion (15) that is conducting and a peripheral portion (13) that is insulated right to a distal end (14) bared, that is to say not insulated, over a few millimeters. The surface C has an area of less than 10 $mm^2$, around 4 $mm^2$, and the surface C' has an area of around 20 $mm^2$.

Thus, the first pole of the electronic stimulation/measurement device is formed by the distal end of the penetrating means (2) of the instrument and the other pole is formed by a reference connection on the patient.

Figure 6:
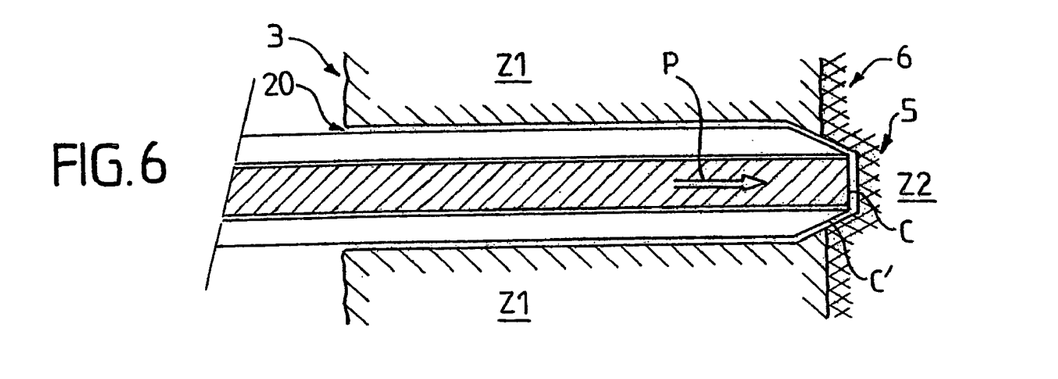
FIG. 6 illustrates a sectional view of the penetration P of the penetrating means of FIG. 3.

In a second embodiment, illustrated in FIGS. 3 and 6 on the one hand and 4 and 7 on the other, said electrodes (5, 6) are each formed by a contact surface C, C' respectively, which is located at the distal end of said penetrating means (2), said contact surfaces C, C' being separated by an insulator (12).

In the version illustrated in FIGS. 3 and 6, the penetrating means (2) comprises a conducting central portion (15) and a conducting outer portion (16), said central portion (15) and said outer portion (16) being separated by a cylindrical insulator (12). The two conducting portions each form one pole of the electronic device.

Thus, the outer portion (16) forms a conducting outer tube, hollow at its center, and the central portion (15) forms a conducting inner cylinder, the central (15) and outer (16) portions both emerging at the end of the penetrating means (2) so as to form the two surfaces C and C' that are isolated from each other.

In this version, the proximal electrode (6) has a contact surface C' greater in area than the contact surface C of the distal electrode (5). The surface C has an area of less than 10 $mm^2$, around 4 $mm^2$, and the surface C' has an area of greater than 100 $mm^2$, around 400 $mm^2$.

Figure 4:
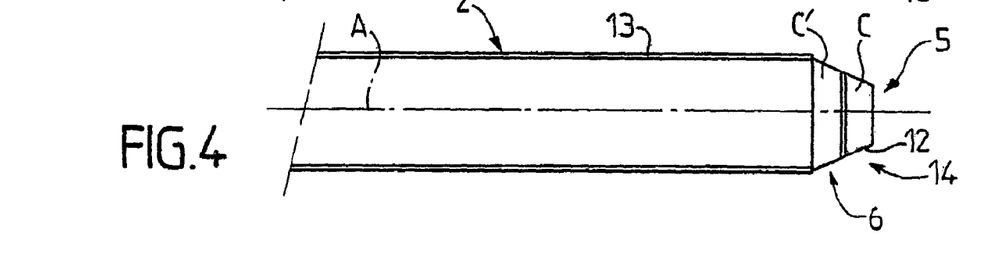
FIG. 4 illustrates a detailed sectional view of another version of the second embodiment of the penetrating means in the form of a probe.
Figure 7:
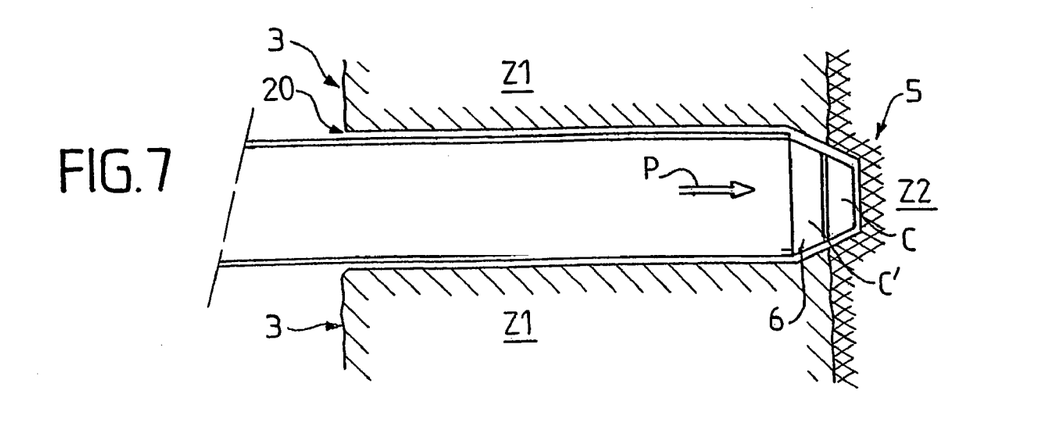
FIG. 7 illustrates a sectional view of the penetration P of the penetrating means of FIG. 4.
Figure 8:
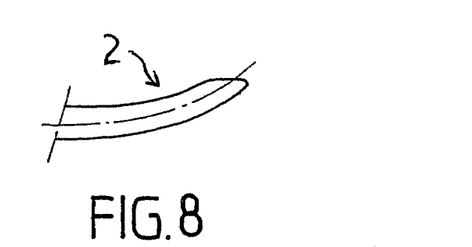
FIGS. 8 and 9 illustrate a front view and top view, respectively, of a penetrating means according to the invention formed by a spatula.
Figure 9:
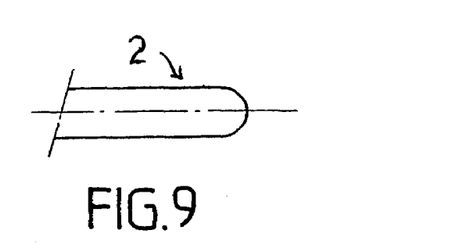
Figure 10:
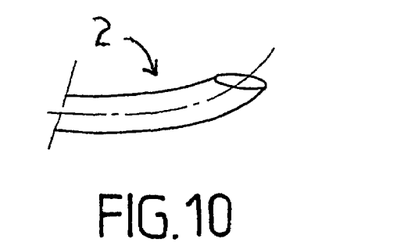
FIGS. 10 and 11 illustrate a front view and a top view, respectively, of a penetrating means according to the invention formed by a curette.
Figure 11:
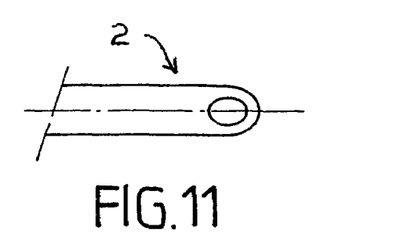

In the version illustrated in FIGS. 4 and 7, the penetrating means (2) comprises an insulating peripheral portion (13) and a noninsulated distal end (14), having two electrodes (5, 6) that are positioned so as to be perpendicular to the axis A of said penetrating means (2) and separated by an insulator (12). The two electrodes (5, 6) each form one pole of the electronic device.

In this version, the electrodes (5, 6) have contact surfaces, C and C' respectively, of approximately the same area, less than 10 $mm^2$ and around 4 $mm^2$. The contact surfaces C, C' are separated by an insulator (12) of thickness less than or equal to 1 mm along an axis A of penetration of said penetrating means (2).

FIGS. 5, 6 and 7 illustrate one moment during the penetration P of the penetrating means (2), during which a change in a physical quantity, and more particularly a change in electrical impedance, is detected by the impedance meter (7). Such a change occurs especially when the penetrating means (2) leaves the cortex of the bone body, represented by the region Z1, and penetrates a soft surrounding tissue, represented by the region Z2.

In the embodiment that combines an impedance meter with an electrostimulator, the stimulation pulses of the device have a waveform, a voltage and an intensity that are known; it is therefore possible to deduce therefrom the impedance measured by the electrodes associated with the device and in particular by the electrodes placed at the distal portion (the tip) of the penetrating means.

This "local impedance" information can then be converted into signals capable of operating the warning device (8).

The penetrating means (2) may have one pair of electrodes or even several pairs of electrodes.

For each pair of electrodes, at least one electrode is positioned at the distal end (14) of said penetrating means (2).

In one embodiment, at least one distal electrode (5) is formed by a contact surface C located on a partial peripheral portion of the distal end of the penetrating means (2) so as to make it possible to detect a change in impedance in a direction approximately perpendicular to the axis A of penetration of the penetrating means (2). Thus, by rotating the penetrating device (2) and, by observing the warning device (8), it is possible to deduce, from the measured change in impedance thanks to this electrode, the configuration of the distal end of the hole (20).

In the section below, the penetrating means (2) is formed by a drill bit.

Figure 12:
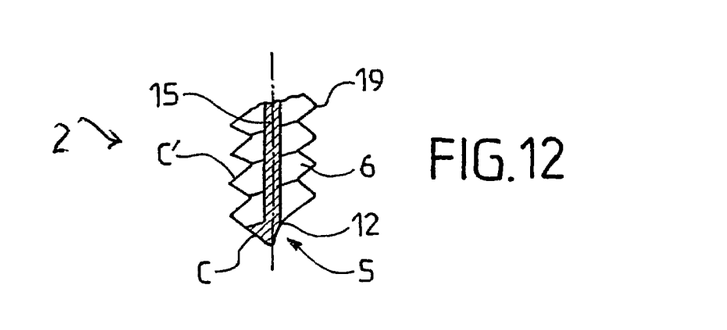
FIG. 12 illustrates a detailed sectional view of a penetrating means according to the invention formed by a drill bit, screw or tap.

The penetrating means (2) is provided, for example, with a helical thread (19) shown in FIG. 12, or with several helical threads, which are formed along the axis A so as to allow holes (20) to be drilled.

The drill bit comprises a conducting central portion (15) and a conducting helical thread (19), the central portion (15) and the helical thread (19) being separated by a cylindrical insulator (12). The two conducting portions each form one pole of the electronic device.

In this version, the proximal electrode (6) has a contact surface C' greater in area than the contact surface C of the distal electrode (5). The surface C has an area of less than 10 $mm^2$, around 4 $mm^2$, and the surface C' has an area of greater than 10 $mm^2$, around 40 $mm^2$. The contact surfaces C, C' are separated by an insulator (12) of thickness less than or equal to 1 mm along an axis A of penetration of said penetrating means (2).

This configuration is also applicable to a screw and especially to a self-drilling screw.

In one embodiment of the invention, the impedance meter (7) and the warning device (8), or the impedance meter (7), the warning device (8) and the electrostimulator (4), are positioned on a removable electronic card (10), visible in FIG. 1, which includes means for connecting said electrodes (5, 6). Thus, the mechanical part of the device (1) can be sterilized in an autoclave, without the electronic part.

It is also possible to provide for the electronic card (10) to be of one-time use—it is delivered in suitable packaging and is fitted by the surgeon into the instrument that he requires (a probe, squared tip, spatula, curette, screw driver, borer, etc.) when he wishes to monitor the progressive penetration of the associated instrument that he is using. The electronic card (10) is thrown away after the operation, whereas the instrument is sterilized.

It is also possible to produce an electronic card (10) that can be sterilized, especially by chemical action.

The electronic card (10) may also be positioned in a casing that preserves sterility.

To allow the electronic card (10) to be fitted into the instrument, the device (1) preferably has a hollow handle (11) into which the electronic card (10) can be placed. Access to the inside of the hollow handle is gained by removing a plug (19).

The connection terminals (18) allow the electrodes to be connected. They may be positioned around the periphery of the handle (11), in order to connect up one or more electrodes, and in the distal portion of the handle relative to the plug (19), in order to allow the electrode(s) located at the distal end of the penetrating means (2) to be connected.

The electronic stimulation/measurement device positioned on the electronic card (10) measures, during use of the instrument, the electrical impedance between the two poles each formed by one electrode and indicates (in an audible, visual or tactile manner) in real time the values and/or changes in said impedance, in particular in the event of the pedicle cortex being breached.

Figure 13:
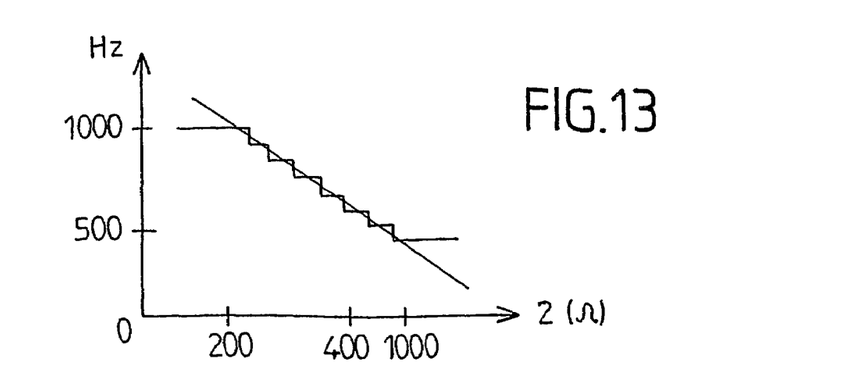
FIG. 13 illustrates two examples of the relationship between the measured impedance Z in ohms and the frequency in hertz of an audible signal emitted by the warning device.

FIG. 13 shows two representations of the relationship between the measured impedance, plotted on the x-axis, and the frequency of an audible signal emitted by the warning device, plotted on the y-axis. This relationship may, for example, be linear, as illustrated by the discontinuous line, or may be stepped. This relationship is obtained with surfaces C and C' about 5 $mm^2$ in area.

In order to use the device according to the invention for boring, it may be useful to provide a number, or set, of penetrating means (2), each penetrating means (2) of which has a different diameter.

The invention has been described above by way of example. Of course, a person skilled in the art is capable of producing various alternative embodiments of the invention without thereby departing from the scope of the patent.

The invention claimed is:

1. A device for creating a cavity in a bony structure having at least two regions of different electrical impedances, said device comprising:
   means for penetrating into said bony structure having said at least two regions of different electrical impedance;
   means for monitoring said penetration of said penetrating means into said bony structure in real-time and for providing an operator with immediate information about passage of a tip of said penetrating means from a first of said regions into a second of said regions;
   said monitoring and information providing means comprising at least two electrodes and at least one impedance meter electrically connected to said at least two electrodes;
   at least one of said electrodes forming a distal end of said penetrating means and forming the tip of said penetrating means;
   said at least one impedance meter continuously receiving signals from the at least two electrodes at least during penetration of said penetrating means into said bony structure so as to continuously measure the impedance between the at least two electrodes during said penetration;
   said monitoring and information providing means further comprising at least one warning device connecting to said at least one impedance meter for receiving signals from the at least one impedance meter during the penetration of said penetrating means; and said at least one warning device having means for generating a warning signal when the tip of the penetrating means with said at least one electrode from said first of said regions having a first electrical impedance to said second of said regions having a second electrical impedance so as to enable the operator to immediately make any needed change in said penetration.

2. The device as claimed in claim 1, wherein said warning signal is a modulated visual warning signal.

3. The device as claimed in claim 1, wherein said warning signal is a frequency-modulated audible warning signal.

4. The device as claimed in claim 1, wherein said warning signal is an intensity-modulated audible warning signal.

5. The device as claimed in claim 4, wherein a proximal electrode has a contact surface greater in area than a contact surface of said at least one electrode forming said distal end of said penetrating means.

6. The device as claimed in claim 1, wherein said warning signal is a frequency-modulated tactile warning signal.

7. The device as claimed in claim 1, wherein said warning signal is an intensity-modulated tactile warning signal.

8. The device as claimed in claim 1, wherein said warning signal is an audible signal having a frequency that is a linear function of the measured impedance.

9. The device as claimed in claim 1, wherein said warning signal is an audible signal having a frequency that is a stepped function of the measured impedance.

10. The device as claimed in claim 1, further including at least one electrostimulator capable of producing a stimulation and able to be connected to the at least two electrodes.

11. The device as claimed in claim 10, wherein at least one first electrode is connected to said at least one electrostimulator and at least one second electrode is connected to an impedance meter.

12. The device as claimed in claim 1, wherein one electrode is formed by a contact surface intended to be positioned on an external surface of an anatomical structure.

13. The device as claimed in claim 1, wherein said electrodes are each formed by a contact surface respectively located at the distal end of said penetrating means, and said contact surfaces being separated by an insulator.

14. The device as claimed in claim 1, wherein the penetrating means comprises a conducting central portion and a conducting outer portion, said conducting central portion and said conducting outer portion being separated by a cylindrical insulator, the conducting outer portion forming a conducting outer tube, hollow at its center, and the conducting central portion forming a conducting inner cylinder, and the conducting central and outer portions both emerging at the end of the penetrating means so as to form two surfaces that are isolated from each other.

15. The device as claimed in claim 1, wherein a proximal electrode has a first contact surface greater in area than a second contact surface of said at least one electrode forming the distal end of said penetrating means and the first contact surface has an area of greater than 10 mm$^2$, and the second contact surface has an area of less than 10 mm$^2$, the contact surfaces being separated by an insulator having a thickness less than or equal to 1 mm along an axis of penetration of said penetrating means.

16. The device as claimed in claim 15, wherein the first contact surface has an area around 40 mm$^2$ and the second contact surface has an area around 4.0 mm$^2$.

17. The device as claimed in claim 1, wherein said at least one electrode forming said distal end of said penetrating means is formed by a contact surface located on a partial peripheral portion of the distal end of the penetrating means for enabling detection of a change in impedance in a direction approximately perpendicular to an axis of penetration of the penetrating means.

18. The drilling device as claimed in claim 1, wherein said device includes means for rotating said penetrating means.

19. The drilling device as claimed in claim 1, wherein the at least one impedance meter, the at least one warning device and optionally an electrostimulator are positioned on a removable electronic card, which card includes means for connecting said electrodes.

20. The drilling device as claimed in claim 19, wherein said device includes a hollow handle for accommodating said electronic card.

21. A drilling device for monitoring the penetration of a penetrating means into a bone structure of a living being having at least two regions of different electrical impedance, said device comprising at least one impedance meter that can be connected to at least two electrodes, at least one of said electrodes being located at a distal end of said penetrating means, said at least one impedance meter continuously measuring the impedance between the at least two electrodes at least during the penetration and at least one warning device delivering a signal indicating at least one of values and changes in the impedance detected due to a change in media by the at least one impedance meter during the penetration of said penetrating means, said signal being modulated proportionally with the changes in the impedance which are detected, at least one electrostimulator capable of producing a stimulation and able to be connected to the at least two electrodes, and wherein neuromuscular stimulation produced by the at least one electrostimulator has a frequency of less than or equal to 10 Hz, a voltage of less than or equal to 4 volts, and a pulse of duration of less than or equal to 400 µs.

22. A system for drilling a cavity in a bony structure having at least two regions of different electrical impedances, said system comprising:

a device for creating said cavity in said bony structure;

said device comprising means for penetrating into said bony structure having said at least two regions of different electrical impedance and means for monitoring said penetration of said penetrating means into said bony structure in real-time and for providing an operator with immediate information about passage of a tip of said penetrating means from a first of said regions into a second of said regions;

said monitoring and information providing means comprising at least two electrodes and at least one impedance meter electrically connected to said at least two electrodes;

at least one of said electrodes forming a distal end of said penetrating means and forming the tip of said penetrating means;

said at least one impedance meter continuously receiving signals from the at least two electrodes at least during penetration of said penetrating means into said bony structure so as to continuously measure the impedance between the two electrodes during said penetration;

said monitoring and information providing means further comprising at least one warning device connected to said at least one impedance meter for receiving signals from the at least one impedance meter during the penetration of said penetrating means; and said at least one warning device having means for generating a warning signal when the tip of the penetrating means with said at least one electrode moves from said first of said regions having a first electrical impedance to said second of said regions having a second electrical impedance so as to enable an operator to immediately make any needed change in said penetration.

23. The system of claim 22 wherein the penetrating means is selected from the group consisting of a fixed penetrating means and a probe, a squared tip, a spatula, a curette, a rotatable penetrating device, a drill screw, and a drill bit.

24. A manual or motor-operated drilling instrument for drilling a cavity in a vertebral pedicle having at least two regions of different electrical impedances, said instrument comprising a device for creating a cavity in said vertebral pedicle, said device comprising:
   a means for penetrating into said vertebral pedicle having said at least two regions of different electrical impedances and means for monitoring the penetration of said penetrating means into said vertebral pedicle in real-time and for providing an operator with immediate information about passage of a tip of said penetrating means from a first of said regions into a second of said regions;
   said monitoring and information providing means comprising at least two electrodes and at least one impedance meter electrically connected to said at least two electrodes;
   at least one of said electrodes forming a distal end of said penetrating means and forming the tip of said penetrating means;
   said at least one impedance meter continuously receiving signals from the at least two electrodes at least during penetration of said penetrating means into said vertebral pedicle so as to continuously measure the impedance between the two electrodes during said penetration;
   said monitoring and information providing means further comprising at least one warning device connected to said at least one impedance meter for receiving signals from the at least one impedance meter during the penetration of said penetrating means; and
   said at least one warning device having means for generating a warning signal when the tip of the penetrating means with said at least one electrode moves from said first of said regions having a first electrical impedance to said second of said regions having a second electrical impedance so as to enable an operator to immediately make any needed change in said penetration.

25. In combination, an electronic card and a device for creating a cavity in a bony structure having at least two regions of different electrical impedances, wherein said device comprises:
   means for penetrating into said bony structure having said at least two regions of different electrical impedance and means for monitoring said penetration of said penetrating means into said bony structure in real-time and for providing an operator with immediate information about passage of a tip of said penetrating means from a first of said regions into a second of said regions;
   said monitoring and information providing means comprising at least two electrodes and at least one impedance meter electrically connected to said at least two electrodes;
   at least one of said electrodes forming a distal end of said penetrating means and forming the tip of said penetrating means;
   said at least one impedance meter continuously receiving signals from the at least two electrodes at least during penetration of said penetrating means into said bony structure so as to continuously measure the impedance between the two electrodes during said penetration;
   said monitoring and information providing means further comprising at least one warning device connected to said at least one impedance meter for receiving signals from the at least one impedance meter during the penetration of said penetrating means; and
   said at least one warning device having means for generating a warning signal when the tip of the penetrating means with said at least one electrode moves from said first of said regions having a first electrical impedance to said second of said regions having a second electrical impedance so as to enable an operator to immediately make any needed change in said penetration;
   wherein the at least one impedance meter, the at least one warning device and optionally an electrostimulator are positioned on said electronic card, and
   wherein said electronic card includes means for connecting said at least two electrodes.

26. The combination as claimed in claim 25, wherein said electronic card can be sterilized.

27. The combination as claimed in claim 26, wherein said card is positioned in a casing that preserves sterility.

28. A device for creating a cavity in a bony structure having at least two regions of different electrical impedances, said device comprising:
   means for penetrating into said bony structure having said at least two regions of different electrical impedance;
   means for monitoring said penetration of said penetrating means into said bony structure in real-time and for providing an operator with immediate information about passage of a tip of said penetrating means from a first of said regions into a second of said regions;
   said monitoring and information providing means comprising at least two electrodes and at least one impedance meter electrically connected to said electrodes;
   at least one of said electrodes forming a distal end of said penetrating means and forming the tip of said penetrating means;
   said at least one impedance meter continuously receiving signals from the at least two electrodes during penetration of said penetrating means into said bony structure so as to continuously measure the impedance between the two electrodes during said penetration;
   said monitoring means further comprising at least one warning device connected to said at least one impedance meter for receiving signals from the at least one impedance meter during said penetration of said penetrating means; and
   said at least one warning device having means for generating a modulated signal from the start of a change in measured impedance and/or when a threshold of a change in the measured impedance is exceeded.

* * * * *

UNITED STATES PATENT AND TRADEMARK OFFICE
Certificate

Patent No. 7,580,743 B2                                Patented: August 25, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Maurice Bourlion, Saint-Chamond (FR); Alain Vanquaethem, Rognes (FR); and Ciaran Bolger, Dublin (IE).

Signed and Sealed this Thirteenth Day of November 2012.

<div align="right">

CHARLES A. MARMOR, II
*Supervisory Patent Examiner*
Art Unit 3735
Technology Center 3700

</div>